United States Patent [19]

Yoshimoto et al.

[11] 4,264,777
[45] Apr. 28, 1981

[54] HERBICIDAL DIPHENYL ETHER COMPOUND

[75] Inventors: Takeo Yoshimoto, Yokohama; Takayuki Inoue; Hideo Michiyama, both of Omuta; Takeo Harayama, Kamakura; Osamu Morikawa; Yoshikata Hojo, both of Chigasaki; Takao Baba, Omuta; Teruhiko Toyama, Fujisawa; Masaaki Ura, Yokohama; Yoshio Takasawa, Chigasaki, all of Japan

[73] Assignee: Mitsui Toatsu Chemicals, Inc., Tokyo, Japan

[21] Appl. No.: 638,109

[22] Filed: Dec. 5, 1975

[30] Foreign Application Priority Data

Dec. 23, 1974 [JP] Japan .................... 49-146789

[51] Int. Cl.³ .................... C07C 43/263; A01N 31/00
[52] U.S. Cl. .................... 568/586; 71/124
[58] Field of Search .................... 260/613 R; 568/586

[56] References Cited

U.S. PATENT DOCUMENTS

| 2,988,571 | 6/1961 | MacFie et al. ............ 260/613 R |
| 3,294,847 | 12/1966 | Albright et al. ........... 260/613 R X |
| 3,376,281 | 4/1968 | Cox et al. ............ 260/613 D X |
| 3,562,335 | 2/1971 | Gildersleve ............ 260/613 R |
| 3,776,961 | 12/1973 | Theissen ............ 260/613 R |
| 3,798,276 | 3/1974 | Bayer ............ 260/612 R |
| 3,849,503 | 11/1974 | Shigehara et al. ............ 260/613 R |
| 3,888,932 | 6/1975 | Bayer et al. . |
| 3,928,416 | 12/1975 | Boyer et al. ............ 560/21 |
| 3,969,102 | 7/1976 | Yoshimoto et al. ............ 260/613 R |
| 4,062,896 | 12/1977 | Yoshimoto et al. . |
| 4,093,446 | 6/1978 | Bayer et al. . |

FOREIGN PATENT DOCUMENTS

| 45-28198 | 9/1970 | Japan . |
| 49-236 | 1/1974 | Japan . |
| 50-37740 | 7/1975 | Japan . |

*Primary Examiner*—Bernard Helfin
*Attorney, Agent, or Firm*—Fisher, Christen & Sabol

[57] ABSTRACT

Nitrodiphenyl ether derivatives of the general formula:

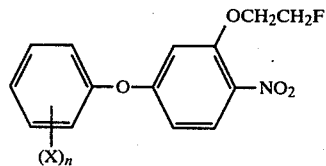

wherein X represents chlorine, fluorine, methyl or trifluoromethyl and n is an integer of 1–3 are valuable as herbicides, the compounds and compositions containing these compounds possessing an excellent herbicidal activity to a wide variety of undesirable weeds with an extremely low toxicity to useful crops.

1 Claim, No Drawings

HERBICIDAL DIPHENYL ETHER COMPOUND

BACKGROUND OF THE INVENTION

1. Field of the Invention

This invention relates to new compounds of the diphenyl ether series possessing a very strong and selective herbicidal activity and to herbicidal compositions containing the new compounds as an active ingredient.

2. Description of the Prior Art

Many compounds of the diphenyl ether series have previously been examined to determine their effectiveness in practical use as herbicides. In many cases, the presence or absence, degree, mode of function, selectivity and duration of the herbicidal activities of these compounds differ with even a slight difference in chemical structure of the compounds such as type, number and position of substituents. Thus, it is extremely difficult to estimate or predict the herbicidal activity of these compounds from their similarities in chemical structure.

It is a well-known fact that some compounds of the diphenyl ether series are excellent herbicides. For example, 2,4-dichlorophenyl-4-nitrophenyl ether (referred to hereinafter as NIP) and 2,4,6-trichlorophenyl-4-nitrophenyl ether (referred to hereinafter as CNP) are widely used as herbicides in rice fields.

Ideal herbicides are required to exhibit on the one hand a very strong herbicidal activity to undesirable plants even at a low level of concentration and on the other hand an extremely low toxicity to useful plants. However, known herbicides developed hitherto still fail to meet fully either or both of these requirements. In recent years, the problem of environmental pollution has been raised in connection with the use of agricultural agents and the use of highly effective herbicides in small amounts has been recommended to minimize any possible environmental effect. Under these circumstances, there is a great demand for developing a new type of herbicide which fully meets the aforesaid requirements.

SUMMARY OF THE INVENTION

Accordingly, it is an object of this invention to provide a new class of diphenyl ether compounds selectively possessing a very strong herbicidal activity with only a slight toxicity to useful plants.

It is another object of this invention to provide herbicidal compositions containing one or more of the new diphenyl ether compounds as an active ingredient.

These and other objects, features and advantages of this invention will become more apparent from the following description.

It has now been found that a certain class of diphenyl ether compounds exhibits excellent herbicidal characteristics and fully meets the aforesaid requirements.

In accordance with this invention, there is provided a new herbicidally active diphenyl ether compound of the general formula:

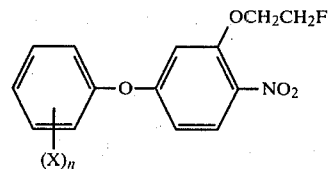

wherein X represents chlorine, fluorine, methyl or trifluoromethyl and n is an integer of 1–3.

DESCRIPTION OF THE PREFERRED EMBODIMENTS

Illustrative of the new compounds of the present invention are:

2,4-dichlorophenyl-4-nitro-3-($\beta$-fluoroethoxy)phenyl ether (m.p. 100°–101° C.)

2,4-dichloro-6-fluorophenyl-4-nitro-3-($\beta$-fluoroethoxy)phenyl ether (m.p. 76°–77° C.)

2,4,6-trichlorophenyl-4-nitro-3-($\beta$-fluoroethoxy)phenyl ether (m.p. 117.5°–118.5° C.)

2-methyl-4-chlorophenyl-4-nitro-3-($\beta$-fluoroethoxy)phenyl ether (m.p. 88°–89° C.)

2-chloro-4-trifluoromethylphenyl-4-nitro-3-($\beta$-fluoroethoxy)phenyl ether (m.p. 98.5°–99° C.)

2-chlorophenyl-4-nitro-3-($\beta$-fluoroethoxy)phenyl ether (m.p. 110°–110.5° C.)

These new diphenyl ether compounds can be prepared by a simple one-step reaction which comprises reacting a compound of the general formula:

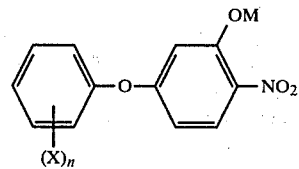

wherein X and n have the same meanings as given above and M represents sodium or potassium, with a compound of the general formula:

wherein Hal represents chlorine or bromine. The reaction is carried out at an elevated temperature, e.g., from 80° to 140° C., with stirring using dimethylformamide as a solvent. The end product is purified by recrystallization from mixed n-hexane-benzene.

The diphenyl ethers of the present invention are suitable both as preemergence and postemergence herbicides. Preemergence herbicides are used to treat the medium in which the desired crop is to be grown by application either before seeding, during seeding, or after seeding and before the crop emerges. Postemergence herbicides are applied after the plants have emerged and during their growth period.

The crops on which the diphenyl ethers of the present invention can be advantageously employed include, for example, cotton, soybeans, peanuts, safflower, beans, peas, carrots, corn, wheat and other cereal crops, and they are especially useful for controlling weeds in rice crops. In transplanted rice crops, the ethers can be applied either preemergence or postemergence to the weeds, i.e., to the growth medium of the transplanted plants either before the weed plants have emerged or while they are in their early leaf stages, or to the growth medium either before or after the rice has been transplated therein.

The diphenyl ethers of the present invention can be applied to any amount which will give the required control of weeds. A preferred rate of application of the herbicides is from about 1 to 50, and preferably from 3 to about 30 grams of the active ingredient per are. For some purposes, the herbicides may be incorporated into the soil or other growth medium prior to planting a crop, and this may be carried out by any convenient means, such as by simple mixing with the soil, application to the surface of the soil and then disking or dragging into the soil to the desired depth, or by employing a liquid carrier to accomplish the necessary penetration and impregnation.

The diphenyl ether may be used without a vehicle or carrier as a herbicide but, in general, it is used as a component in a herbicidal composition with a suitable carrier, i.e., a substance which will dissolve, disperse or diffuse the herbicide without detrimental effect to the herbicide, the desired crop or the environment. For example, it is dissolved in or dispersed into an appropriate liquid vehicle such as an organic solvent, or alternatively mixed with or adsorbed on an appropriate inert solid carrier such as a diluent or weighting agent. The herbicides may be used in various forms such as an emulsifiable concentrate, wettable powder, granular formulation, dust, aerosol, etc., if necessary by mixing the herbicides with an adjuvant such as an emulsifier, stabilizer, dispersing agent, suspending agent, vehicle, wetting agent or permeating agent. Preferred examples of the liquid vehicle include one or more of alcohols, naphtha, aliphatic and aromatic hydrocarbons and the like while preferred examples of the inert solid carrier include mineral powders such as talc, bentonite and other clays, etc. and insoluble inorganic compounds such as calcium carbonate, silica, etc.

The herbicides of this invention may contain a mixture of at least two active ingredients and may be used in combination with one or more other agricultural agents including other herbicides, insecticides, sterilizers and plant growth controlling agents, soil-improving agents and fertilizers. It is also possible to manufacture preparations containing the herbicides of this invention in combination with these agricultural agents. Examples of other kinds of herbicides which may be used jointly with the herbicides of this invention may include those of the urea series, thiolcarbamate series, organophosphorus series, acid amide series, triazine series and aryloxyfatty acid series.

The concentration of the active ingredients in the herbicidal compositions of this invention is preferably from 1% to 10% in the case of granular formulations, from 40% to 80% in the case of wettable powders and from 10% to 50% in the case of emulsifiable concentrates, all percentages being by weight.

In comparison with NIP or CNP, the active ingredients of this invention exhibit excellent herbicidal activity to barnyard grass and other kinds of weeds. The herbicidal activity is not weakened to any great extent when the active ingredients are diluted to a low concentration. In addition, the active ingredients of this invention exhibit a prolonged durability in herbicidal activity and have little harmful effects upon useful crops.

This invention will now be explained in more detail by way of the following illustrative examples wherein all parts and percentages are by weight unless otherwise indicated.

EXAMPLE 1

Preparation of the β-fluoroethoxy-nitrodiphenyl ethers (a) 2,4-Dichlorophenyl-4-nitro-3-(β-fluoroethoxy)phenyl ether In a 200 ml. flask equipped with a stirrer, a thermometer, a condenser and an inlet for starting materials were placed 80 grams of dimethylformamide and 15.0 grams of the potassium salt of 2,4-dichlorophenyl-4-nitro-3-hydroxyphenyl ether (0.0465 mol). Then the mixture was warmed to 125°–130° C. and 128 grams of 1-chloro-2-fluoroethane (0.155 mol) was added dropwise for 60 minutes with stirring while maintaining the temperature of the flask contents. The reaction was then continued for 4 hours with stirring within the same temperature range. After transfer of the reaction mixture to a distillation flask, dimethylformamide was removed by steam distillation leaving a distillation residue which was then extracted with 150 ml. of benzene. The benzene phase was washed with 150 ml. of a 1% aqueous solution of sodium hydroxide and then with water thoroughly until the aqueous phase became neutral. The benzene phase was allowed to stand and then separated. After dehydration of the benzene phase with anhydrous sodium sulfate, benzene was removed by distillation leaving 14.0 grams of a solid substance. The solid substance was dissolved in a mixed n-hexane-benzene solvent by warming and then cooled to effect recrystallization whereby 5.2 grams of 2,4-dichlorophenyl-4-nitro-3-(β-fluoroethoxy)phenyl ether (Compound 1) were obtained in the form of crystals. The melting point and elementary analysis of the $C_{14}H_{10}Cl_2FNO_4$ compound are shown in the following Table 1.

(b) Other compounds represented by the above general formula (I) were also prepared in a similar manner to that described in (a) above. Typical other compounds (Compounds 2–6) and their characteristics are also shown in the following Table 1.

TABLE 1

General Formula (I): (phenyl)(X)$_n$—O—(phenyl with OCH$_2$CH$_2$F and NO$_2$)

| Compound No. | (X)$_n$ | M.P. (°C.) | Elementary Analysis (%) Found/[Calc.] | | | | |
|---|---|---|---|---|---|---|---|
| | | | C | H | N | Cl | F |
| 1 | Cl, Cl (2,4-dichlorophenyl) | 100–101 | 45.87 [48.58] | 2.94 [2.91] | 4.12 [4.05] | 20.57 [20.49] | 5.14 [5.49] |

TABLE 1-continued

General Formula (I):  Ar—O—(phenyl with OCH$_2$CH$_2$F and NO$_2$), Ar = (X)$_n$-substituted phenyl

| Compound No. | (X)$_n$ | M.P. (°C.) | Elementary Analysis (%) Found/[Calc.] | | | | |
|---|---|---|---|---|---|---|---|
| | | | C | H | N | Cl | F |
| 2 | Cl, Cl, F (dichloro-fluoro phenyl) | 76–77 | 46.19 [46.17] | 2.44 [2.49] | 4.01 [3.85] | 19.58 [19.47] | 10.36 [10.44] |
| 3 | Cl, Cl, Cl (trichlorophenyl) | 117.5–118.5 | 44.52 [44.18] | 2.61 [2.38] | 3.83 [3.68] | 28.01 [27.95] | 5.32 [5.00] |
| 4 | Cl, CH$_3$ | 88–89 | 55.62 [55.31] | 4.13 [4.02] | 4.43 [4.30] | 10.66 [10.89] | 5.47 [5.83] |
| 5 | Cl, CF$_3$ | 98.5–99 | 47.80 [47.45] | 2.65 [2.65] | 3.63 [3.69] | 9.39 [9.34] | 19.87 [20.02] |
| 6 | Cl | 110–110.5 | 53.22 [53.94] | 3.57 [3.56] | 4.36 [4.49] | 11.29 [11.38] | 6.32 [6.10] |

EXAMPLE 2

Granular Formulation 1

4 Parts of Compound 1, 73 parts of bentonite, 20 parts of talc, 2 parts of sodium dodecylbenzenesulfonate and 1 part of sodium ligninesulfonate were mixed and kneaded with an appropriate amount of water. The mixture was shaped into granules by a conventional method using an extruding pelletizer whereby 100 parts of a granular preparation were obtained.

EXAMPLE 3

Granular Formulation 2

One part of Compound 2, 80 parts of bentonite, 17 parts of talc, 1 part of polyoxyethyleneglycol monolaurate and 1 part of sodium naphthalenesulfonate were mixed and kneaded with an appropriate amount of water. The mixture was then shaped into granules by a conventional method using an extruding pelletizer whereby 100 parts of a granular preparation were prepared.

EXAMPLE 4

Wettable Powder 1

50 Parts of Compound 3, 40 parts of talc, 7 parts of sodium laurylsulfate and 3 parts of sodium alkylnaphthalenesulfonate were mixed and then pulverized to prepare 100 parts of a wettable powder.

EXAMPLE 5

Wettable Powder 2

50 Parts of Compound 5, 40 parts of diatomaceous earth and 10 parts of sodium dodecylbenzenesulfonate were mixed and then pulverized to prepare 100 parts of a wettable powder.

EXAMPLE 6

Emulsifiable Concentrate

10 Parts of Compound 4, 10 parts of Solpor 800 A (an emulsifier manufactured by Toho Chemicals, Co., Ltd.) and 80 parts of solvent naphtha were mixed to prepare 100 parts of a stock solution for forming an emulsion.

EXAMPLE 7

Evaluations of Herbicidal Effects 3.5 Kg. of an air-dried fine soil (which passed through a sieve of 14 mesh) from a crop farm were placed in each of 1/5,000 are (0.02 m$^2$) Wagner pots, to which one gram each of N, P$_2$O$_5$ and K$_2$O was evenly added in the form of chemical fertilizers. The water content in the soil was regulated to 60% of the maximum capacity therefor and then the soil in the pots was sown with a definite quantity of seeds of the respective crop to be tested. The seeds were covered with the soil. An emulsion of each compound to be tested was prepared according to the method described in Example 6 and a given amount of the emulsion was diluted with water and applied to the pots in an amount equivalent to 10 liters per are (0.01 hectare). The soil in each pot was evenly treated with the respective diluted emulsion by the aid of a pippette and then allowed to stand in a greenhouse to permit growth of the crops.

One month after the treatment the growth of the crops and the emergence of weeds was observed and the results tabulated in Table 2 were obtained. A comparison of the state of growth of the crops and the state of emergence of weeds in the treated areas was made with those in an untreated area and the herbicidal effect was classified into 6 grades from "O" indicating no suppression of growth to "5" indicating perfect (100%)

suppression of growth. The herbicidal effect was evaluated in the same manner for all of the following Tables 2-5.

TABLE 2

| Compound tested | Amount used (Active ingredient grams/are) | Rice | Soybean | Corn | Crabgrass | Barnyard grass | Lambs quarter | Redroot pigweed |
| --- | --- | --- | --- | --- | --- | --- | --- | --- |
| Compound 1 | 10 | 0 | 0 | 0 | 5 | 4 | 4 | 4 |
|  | 20 | 0 | 0 | 0 | 5 | 5 | 5 | 5 |
|  | 50 | 1 | 0 | 0 | 5 | 5 | 5 | 5 |
| Compound 2 | 5 | 0 | 0 | 0 | 5 | 5 | 5 | 5 |
|  | 10 | 0 | 0 | 0 | 5 | 5 | 5 | 5 |
|  | 20 | 1 | 0 | 1 | 5 | 5 | 5 | 5 |
| Compound 5 | 2 | 0 | 0 | 0 | 5 | 5 | 5 | 5 |
|  | 5 | 0 | 0 | 0 | 5 | 5 | 4 | 5 |
|  | 10 | 0 | 0 | 0 | 5 | 5 | 5 | 5 |
| NIP E.C. (Comparative) | 10 | 0 | 0 | 0 | 2 | 2 | 3 | 2 |
|  | 20 | 1 | 0 | 0 | 3 | 3 | 4 | 3 |
|  | 50 | 2 | 1 | 1 | 4 | 5 | 4 | 4 |
| CNP E.C. (Comparative) | 10 | 0 | 0 | 0 | 1 | 1 | 2 | 1 |
|  | 20 | 1 | 0 | 0 | 3 | 2 | 3 | 2 |
|  | 50 | 1 | 1 | 1 | 4 | 4 | 4 | 3 |

EXAMPLE 8

3.3 Kg of an air-dried soil (which passed through a sieve of 14 mesh) from a rice field including seeds of common rice field weeds in a naturally mixed state were placed in each of 1/5,000 are (0.02 m$^2$) Wagner pots to which 0.8 gram each of N, P$_2$O$_5$ and K$_2$O was evenly added in the form of chemical fertilizers. The soil was mixed with an appropriate amount of water, and the level of the water was maintained above that of the soil. Three rice seedlings (2.0 leaf stage) which had been grown in a greenhouse were planted in each pot and were grown in a greenhouse. The weeds began to sprout five days after transplantation of the rice. Then, a given amount of a compound to be tested was added in the form of a wettable agent prepared according to the method described in Example 4 or 5 to each respective pot where the level of water was maintained above that of the soil.

One month after the treatment, the states of growth of the rice and weeds were observed and the results tabulated in Table 3 were obtained. During the test period, the depth of water in the pots was at all times maintained at 3 cm.

In each of the following Tables 3, 4 and 4A, the broadleaved weeds were *Monochoria vaginalis, Alisma canaliculatum, Rotala indica* and *Lindermia procumbens* and the narrow-leaved weeds were *Cyperus difformis, Eleocharis acicularis* and *Scirpus hotauri*.

TABLE 3

| Compound tested | Amount used (Active Ingredient grams/are) | Rice | Barnyard grass (Echinochloa crus-galli) | Other common weeds Broad-leaved | Narrow-leaved |
| --- | --- | --- | --- | --- | --- |
| Compound 1 | 5 | 0 | 5 | 5 | 5 |
|  | 10 | 0 | 5 | 5 | 5 |
|  | 20 | 0 | 5 | 5 | 5 |
| Compound 2 | 1 | 0 | 5 | 5 | 5 |
|  | 2 | 0 | 5 | 5 | 5 |
|  | 5 | 1* | 5 | 5 | 5 |
| Compound 3 | 5 | 0 | 5 | 5 | 5 |
|  | 10 | 0 | 5 | 5 | 5 |
|  | 20 | 0 | 5 | 5 | 5 |
| Compound 4 | 5 | 0 | 4 | 5 | 4 |
|  | 10 | 0 | 5 | 5 | 5 |
|  | 20 | 0 | 5 | 5 | 5 |

TABLE 3-continued

| Compound tested | Amount used (Active Ingredient grams/are) | Rice | Barnyard grass (Echinochloa crus-galli) | Other common weeds Broad-leaved | Narrow-leaved |
| --- | --- | --- | --- | --- | --- |
| Compound 5 | 1 | 0 | 5 | 5 | 5 |
|  | 2 | 0 | 5 | 5 | 5 |
|  | 5 | 1* | 5 | 5 | 5 |
| Compound 6 | 5 | 0 | 2 | 4 | 4 |
|  | 10 | 0 | 3 | 4 | 4 |
|  | 20 | 0 | 5 | 5 | 5 |
| NIP Gran. (Comparative) | 5 | 0 | 1 | 2 | 2 |
|  | 10 | 1* | 2 | 3 | 3 |
|  | 20 | 2* | 4 | 4 | 4 |
| CNP Gran. (Comparative) | 5 | 0 | 1 | 2 | 1 |
|  | 10 | 1* | 2 | 3 | 3 |
|  | 20 | 1* | 4 | 4 | 4 |

*Leaf sheaths and leaf blades turned brown due to phytotoxicity of the compound.

EXAMPLE 19

3.3 Kg of an air-dried soil (which passed through a sieve of 14 mesh) from a rice field including seeds of common rice field weeds in a naturally mixed state were placed in each of 1/5,000 are (0.02 m$^2$) Wagner pots to which 0.8 gram each of N, P$_2$O$_5$ and K$_2$O was evenly added in the form of chemical fertilizers. The soil was mixed with an appropriate amount of water, and the level of the water was maintained above that of the soil. A given amount of a respective compound to be tested was added to each of the several pots in the form of an emulsion prepared according to the method described in Example 6 and the compound was homogeneously mixed with the soil to a depth of 5 cm. (Table 4) or, alternatively, the emulsion was added dropwise by the aid of a pippette to the water covering the soil (Table 4A). Three rice seedlings (3.0 leaf stage) were planted in each pot wherein the depth of water covering the soil was 3 cm. The seedlings were allowed to grow in a greenhouse.

One month after the treatment, any influence on the compounds on the rice and the state of emergence or growth of the weeds were observed and the results are shown in Tables 4 and 4A.

TABLE 4

Incorporated into the soil to a depth of 5 cm.

| Compound tested | Amount used (Active Ingredient grams/are) | Rice | Barnyard grass (Echinochloa crus-galli) | Broad-leaved | Narrow-leaved |
|---|---|---|---|---|---|
| Compound 1 | 5 | 0 | 5 | 5 | 5 |
|  | 10 | 0 | 5 | 5 | 5 |
|  | 20 | 0 | 5 | 5 | 5 |
| Compound 2 | 1 | 0 | 5 | 5 | 5 |
|  | 2 | 0 | 5 | 5 | 5 |
|  | 5 | 0 | 5 | 5 | 5 |
| Compound 5 | 1 | 0 | 5 | 5 | 5 |
|  | 2 | 0 | 5 | 5 | 5 |
|  | 5 | 0 | 5 | 5 | 5 |
| NIP E.C. (Comparative) | 5 | 0 | 0 | 0 | 0 |
|  | 10 | 1* | 2 | 3 | 2 |
|  | 20 | 2* | 4 | 4 | 3 |
| CNP E.C. (Comparative) | 5 | 0 | 0 | 0 | 0 |
|  | 10 | 1* | 2 | 3 | 2 |
|  | 20 | 2* | 3 | 4 | 3 |

*Leaf sheaths and leaf blades turned brown due to phytotoxicity of the compound.

TABLE 4A

Applied to the water covering the soil surface

| Compound tested | Amount used (Active Ingredient grams/are) | Rice | Barnyard grass (Echinochloa crus-galli) | Broad-leaved | Narrow-leaved |
|---|---|---|---|---|---|
| Compound 1 | 5 | 0 | 5 | 5 | 5 |
|  | 10 | 0 | 5 | 5 | 5 |
|  | 20 | 0 | 5 | 5 | 5 |
| Compound 2 | 1 | 0 | 5 | 5 | 5 |
|  | 2 | 0 | 5 | 5 | 5 |
|  | 5 |  | 5 | 5 | 5 |
| Compound 5 | 1 | 0 | 5 | 5 | 5 |
|  | 2 | 0 | 5 | 5 | 5 |
|  | 5 | 0 | 5 | 5 | 5 |
| NIP E.C. (Comparative) | 5 | 1* | 2 | 2 | 2 |
|  | 10 | 2* | 3 | 3 | 4 |
|  | 20 | 3* | 4 | 4 | 4 |
| CNP E.C. (Comparative) | 5 | 0 | 1 | 1 | 1 |
|  | 10 | 1* | 2 | 3 | 3 |
|  | 20 | 2* | 4 | 4 | 4 |

*Leaf sheaths and leaf blades turned brown due to phytotoxicity of the compound.

EXAMPLE 10

Three days after planting of rice seedlings, the rice field was divided into areas of 10 m². Granules of a compound to be tested were prepared according to the method described in Example 2 or 3 and sprinkled in an amount of 300 grams per are into the water covering the soil. Thirty days after the application, the state of emergence of weeds per 1 m² of the test areas and any phytotoxicity to the rice plants were observed and investigated. The results are shown in Table 5.

TABLE 5

| Compound tested | Amount used (Active ingredient grams/are) | Phytotoxicity to rice | Barnyard-grass (Echinochloa crus-galli) | Monochoria vaginalis | Umbrella sedge (Cyperus difformis) | Bulrush (Scirpus juncoides) | Spike rush (Eleocharis acicularis) |
|---|---|---|---|---|---|---|---|
| Compound 1 (5% granular) | 15 | None | 0 | 0 | 0 | 0 | 0 |
| Compound 2 (2% granular) | 6 | Slight* | 0 | 0 | 0 | 0 | 0 |
| Compound 3 (7% granular) | 21 | None | 0.2 | 0 | 0 | 1 | 0 |
| Compound 5 (1% granular) | 3 | Slight* | 0 | 0 | 0 | 0 | 0 |
| Compound 6 (9% granular) | 27 | None | 17 | 12 | 2.7 | 5 | 6 |
| NIP Granular (Comparative) | 21 | Moderate* | 40 | 16 | 6 | 36 | 11 |
| CNP Granular (Comparative) | 27 | Small* | 31 | 14 | 2 | 29 | 7 |
| Untreated |  | None | 160 | 27 | 31 | 21 | 26 |

*Leaf sheaths and leaf blades turned brown due to phytotoxicity of the compound.

As is evident from the results of the above tests, the herbicides of this invention not only exhibit a very strong herbicidal activity against various undesirable weeds but also have better characteristics than conventional herbicides of the diphenyl ether series in that the lowering of the activity upon dilution is slight and the toxic effect on various useful crops is absent.

What is claimed is:

1. 2-chloro-4-trifluoromethylphenyl-4-nitro-3-($\beta$-fluoroethoxy)phenyl ether.

* * * * *